(12) United States Patent
Seckin

(10) Patent No.: US 9,345,459 B2
(45) Date of Patent: May 24, 2016

(54) SURGICAL ENDOBAG AND METHOD OF APPLICATION THEREOF

(76) Inventor: Tamer A. Seckin, Ankara (TR)

( * ) Notice: Subject to any disclaimer, the term of this patent is extended or adjusted under 35 U.S.C. 154(b) by 402 days.

(21) Appl. No.: 13/813,833

(22) PCT Filed: Aug. 1, 2011

(86) PCT No.: PCT/EP2011/063253
§ 371 (c)(1),
(2), (4) Date: Feb. 1, 2013

(87) PCT Pub. No.: WO2012/016968
PCT Pub. Date: Feb. 9, 2012

(65) Prior Publication Data
US 2013/0138115 A1 May 30, 2013

(30) Foreign Application Priority Data

Aug. 1, 2010 (TR) .................................. 2010/06346
Aug. 1, 2010 (TR) .................................. 2010/06347

(51) Int. Cl.
| A61B 17/24 | (2006.01) |
| A61B 17/26 | (2006.01) |
| A61B 17/00 | (2006.01) |
| A61B 17/12 | (2006.01) |
| A61B 17/42 | (2006.01) |
| A61B 17/02 | (2006.01) |

(52) U.S. Cl.
CPC ........... *A61B 17/00234* (2013.01); *A61B 17/12* (2013.01); *A61B 17/42* (2013.01); *A61B 17/4241* (2013.01); *A61B 46/13* (2016.02); *A61B 17/0218* (2013.01); *A61B 2017/00278* (2013.01); *A61B 2017/00287* (2013.01); *A61B 2217/005* (2013.01)

(58) Field of Classification Search
CPC ................. A61B 17/0218; A61B 2017/00287; A61B 2017/00278; A61B 2017/00557; A61B 17/42; A61B 17/00234; A61M 13/003
USPC .......................................................... 606/114
See application file for complete search history.

(56) References Cited

U.S. PATENT DOCUMENTS

| 3,938,521 A * | 2/1976 | Ritota ..................... A61F 5/455 |
| | | 604/328 |
| 5,176,687 A | 1/1993 | Hasson et al. |
| 5,279,548 A | 1/1994 | Essig et al. |
| 5,370,647 A | 12/1994 | Graber et al. |
| 5,645,083 A * | 7/1997 | Essig et al. ..................... 128/898 |
| 6,270,505 B1 * | 8/2001 | Yoshida ........... A61B 17/00234 |
| | | 606/127 |
| 6,383,195 B1 | 5/2002 | Richard |

OTHER PUBLICATIONS

PCT/EP2011/063253 International Search Report Feb. 9, 2012.

* cited by examiner

*Primary Examiner* — Katherine M Shi
(74) *Attorney, Agent, or Firm* — Hayes Soloway, P.C.

(57) ABSTRACT

An apparatus for transporting body tissue during a pelvic or peritoneal surgery through transvaginal-transdouglas route comprises a bag portion to be placed inside the body of the patient and adapted to receive body tissue to be removed during the surgery, the bag portion has an opening for tissue removal.

5 Claims, 12 Drawing Sheets

SURGICAL ENDOBAG AND METHOD OF APPLICATION THEREOF

CROSS-REFERENCED TO RELATED APPLICATIONS

This application is a National Stage entry of International Application PCT/EP2011/063253, filed Aug. 1, 2011, which claims priority to Turkish Application No. 2010/06347, filed Aug. 1, 2010 and Turkish Application No. 2010/06346, filed Aug. 1, 2010, the disclosure of these prior applications are hereby incorporated in their entirety by reference.

TECHNICAL FIELD

The present invention relates to a surgical method and apparatus for use in connection with examinations and surgical interventions through a hollow organ forming a natural orifice of a human or animal body, preferably through the vagina of a female patient. The present disclosure relates to subject-matter contained in Turkish Utility Model Applications 2010/06346 and 2010/06347 filed on Jan. 8, 2010 which is expressly incorporated herein by reference in its entirety.

BACKGROUND ART

Endoscopy is a minimally invasive diagnostic medical procedure that is used to assess the interior surfaces of an organ by inserting a tube into the body. Endoscopic surgery methods are widely used for treatment of a variety of disorders that were formally treated by conventional surgical techniques. Laparoscopic surgery is an endoscopic surgical technique in which operations in the abdomen or pelvic cavity are performed through small incisions as compared to larger incisions needed in traditional surgical procedures. Natural orifice transluminal endoscopic surgery is a laparoscopic surgery performed with an instrument passed through a natural orifice of the body (mouth, urethra, anus, etc.) then through an internal incision in the stomach, vagina, bladder or colon.

The instrument for natural orifice transluminal endoscopic surgery can comprise a rigid or flexible tube, a light delivery system to illuminate the organ or object under inspection, the light source is normally outside the body and the light is typically directed via an optical fiber system, a lens system transmitting the image to the viewer from the fiberscope, an additional channel to allow entry of medical instruments or manipulators. U.S. Pat. No. 5,279,548 discloses a surgical method and apparatus for use in pelvic surgery where a trocar sleeve is positioned in the vagina of a female patient and then the sleeve is made traverse the vaginal wall behind the cervix of the patient.

Some laparoscopic surgery procedures known in the prior art performed through the vagina and the rectouterine pouch are removal of the gallbladder at the end of endoscopical cholecystectomy, appendicectomies following vaginal hysterectomy, various gynaecological procedures, such as myomectomy and abdominal operations, such as cholecystectomies, colectomies and splenectomies. Natural orifice transluminal endoscopic surgery performed through the rectouterine pouch or any other natural orifice can be applied in combination with open incision surgery or laparoscopic surgery.

The rectouterine pouch is the extension of the peritoneal cavity between the rectum and back wall of the uterus in the female human body. In women it is the deepest point of the peritoneal cavity, behind the uterus and in front of rectum. It is near the posterior fornix of the vagina. The rectouterine pouch is a common site for the spread of pathology such as ascites, tumour, endometriosis, pus, etc. It is also known by the names Douglas pouch, Douglas space, Douglas cul-de-sac. The Rectouterine Pouch can be reached through the posterior fornix of the vagina.

During the operation performed through the Douglas pouch the surgical instruments are first placed in the vagina. The distal end portions of the instruments then have to traverse a portion of the vaginal wall located behind the cervix, the posterior fornix of the vagina in order to penetrate to the rectouterine pouch. This operation is also called transvaginal-transdouglas technique.

When employing transvaginal-transdouglas technique there is an increased risk of inadvertent damage to or dissection into the bladder, ureters, uterine vessels and uterosacral and cardinal ligaments due to inherent limitations on visibility, anatomical identification and the ability to manipulate organs such as uterus. For a secure incision uterine vessels and cardinal/uterosacral ligaments have to be accurately secured by additional instrumentation through additional ports that complicate the operation and prolong the operation time.

Accordingly, there is a need for easy and clean removal of body tissue from the inside of the body to the outside during a surgery.

The present invention provides an apparatus and a method for removal of body tissue during surgery.

In accordance with the present invention, an apparatus comprises an elongated body having an attachment means. The body may be adapted to be received in the vagina of a female patient. The body may be a tube, a trocar sleeve, a barrel, a solid body or a hollow body. The body may be made of metal or plastic or rubber material. The attachment means may be arranged on an inner surface or on an outer surface of the elongated body. The attachment means may be a guiding means, a rail, a groove, a hole or a protrusion. A distal end portion of the elongated body may be oblique and/or rounded, convex, hemispherical or quarter-spherical. The elongated body may comprise an open end and a closed end. The closed end may comprise at least one hole. The closed end may make an angle with the surface of the elongated member which is lower or higher than 90 degrees. The closed end may be formed oblique, hemispherical or quarter-spherical. The elongated body may have channels there trough. The attachment means may be arranged such that a rotatable part is attachable to the attachment means. The rotatable part may be articulated on the elongated body. The rotatable part may be rotated by an operator arm. The rotatable part may have tooth at its end near the articulation point. The operator arm at its distal end may attach to the rotatable part via hinge means or tooth means such that when the operator arm is pulled or pushed with respect to the rotatable part, the rotatable part is rotated about its articulation point. The rotatable part may be the rotatable portion of a uterus manipulator. The attachment means may be arranged such that a uterus manipulator is attachable to the attachment means. The attachment means and the uterus manipulator may be arranged such that a movement of the elongated body with respect to the uterus manipulator causes a rotation of the rotatable part of the uterus manipulator. A uterus manipulator may be positioned in a groove or channel of the apparatus.

In another aspect of the present invention, the apparatus is adapted to be positioned in the vagina of a female patient so that the apparatus is able to traverse a portion of a vaginal wall located behind the cervix of the patient and so that distal end portion of the apparatus is able to penetrate or to be introduced to the rectouterine pouch of a female body.

In yet another aspect of the present invention, there is provided a surgical instrument comprising an elongated part, the elongated part having a rotatable end portion. The rotatable end portion may include an articulation or a hinge about which the rotatable portion is rotatable, preferably a flexible articulation. The surgical instrument may be a uterus manipulator. The surgical instrument may have an attachment means thereon. The attachment means may be a rail or a protrusion or a hollow element. The elongated rod may be adapted to be received into the elongated body or in a groove or in a channel of the elongated body.

In yet another aspect of the present invention, the elongated body of the apparatus and the elongated part of the surgical instrument are arranged parallel to each other such that they are able to move in the longitudinal direction with respect to each other.

In yet another aspect of the present invention, the rotatable portion of the surgical instrument is rotated to a vertical position at about 90 degrees with respect to the elongated body and/or elongated part before the apparatus traverses a portion of a vaginal wall located behind the cervix of the female patient and penetrates to the rectouterine pouch.

In yet another aspect of the present invention, there is provided a sheet member adapted to be placed in a space in the human body. The sheet may be a membrane. The sheet may be a plastic, polymer or nylon sheet. The sheet may be formed as a bag. The sheet or the bag may comprise two separated zones or may comprise at least two separate compartments. The sheet may comprise an opening. An elongated port may be arranged at the opening. The elongated port may comprise at least an open end. The elongated port may be adapted to be received through the vagina of a female patient such that the open end is arranged outside the human body. The sheet may comprise at least an attachment means for fixing the sheet to the inner parts of the human body. The sheet may be under positive or negative gas or liquid pressure with respect to its ambient.

In yet another aspect of the present invention, the sheet or the bag is inserted in a closed configuration through the vagina and the rectouterine pouch into a peritoneal cavity of the patient. The sheet or the bag may be inserted through one of the guides or channels of the apparatus. The sheet or the bag is then opened in a space in the human body. The sheet or bag may be attached and fixed to the inner parts of the human body using the attachment means or pressurized liquid or gaseous medium. The pressurized medium may be introduced through the vagina into the body cavity.

In yet another aspect of the present invention, the pressure above and/or inside the apparatus is set higher than the pressure below and/or outside the apparatus so that the apparatus is placed and fixed inside the human body with the help of the pressure difference. The pressure above and/or inside and/or below and/or outside the sheet is adjusted by a liquid or gaseous medium which is transferred to inside of the human body. The liquid or gaseous medium may be transferred through one of the channels or guides of the apparatus.

In yet another aspect of the present invention, a surgical method for performing examinations and surgical interventions through the vagina and the rectouterine pouch of a female patient comprises the steps of providing a tube adapted to receive one or more surgical instruments there through and having a distal end with an oblique profile such that the distal end of the tube is inclined making an oblique angle with the longitudinal axis of the tube forming a nose at the distal end of the tube, positioning the tube in the vagina of the patient such that the tube traverses a portion of a vaginal wall located behind the cervix of the patient so that the distal end of the tube penetrates to the rectouterine pouch.

According to another feature of the present invention the method further comprises the step of positioning the tube in the vagina such that the shortest longitudinal side of the tube faces the uterus of the patient and such that the nose at the distal end of the tube clears the penetration way of the tube.

According to another feature of the present invention the method further comprises the steps of providing an elongated housing, positioning the tube in the housing in a telescopically movable manner, preferably before positioning the tube in the vagina.

According to another feature of the present invention a method comprises the steps of providing a uterus manipulator having a rotatable distal end, positioning the uterus manipulator longitudinally parallel to and movable with respect to a tube in the vagina of the patient, placing the distal end of the uterus manipulator in the uterus and repositioning the uterus using the rotatable distal end of the uterus manipulator to an appropriate position before the tube traverses the vaginal wall such that the penetration way of the tube is cleared from obstacles and the posterior fornix of the vagina is visible through the vagina and an incision can be made in the posterior fornix of the vagina.

According to another feature of the present invention the method further comprises the step of positioning the uterus manipulator in the housing in a telescopically movable manner, preferably before positioning the tube and the uterus manipulator in the vagina.

According to another feature of the present invention the method further comprises the step of locking the tube and/or the uterus manipulator in the housing such that the tube and/or uterus manipulator can not be moved telescopically in the housing.

According to another feature of the present invention the method further comprises the steps of repositioning the uterus by tilting the rotatable distal end of the uterus manipulator to a position where the distal end of the uterus manipulator makes an angle 0 to 140 degree with the longitudinal axis of the tube, the angle being preferably about 90 degree and locking the rotatable end of the uterus manipulator at the position.

In accordance with an alternative embodiment of the present invention a surgical method for performing examinations and surgical interventions through the vagina and the rectouterine pouch of a female patient comprising the steps of providing a tube adapted to receive one or more surgical instruments therethrough and having a distal end and a uterus manipulator positioned longitudinally parallel to and movable with respect to the tube, the uterus manipulator having a rotatable distal end, positioning the tube and the uterus manipulator in the vagina of the patient, placing the distal end of the uterus manipulator in the uterus and repositioning the uterus using the rotatable distal end of the uterus manipulator to a position such that the penetration way of the tube is cleared from obstacles, preferably to a position where the longitudinal axis of the uterus body makes an angle with the longitudinal axis of the vagina, the angle being between 0 to 140 degrees, preferably the angle being 90 degrees, performing an incision in the vaginal wall, preferably at the posterior fornix of the vagina and, moving the tube in the vagina with respect to the uterus manipulator in a forward direction such that the tube traverses a portion of a vaginal wall located behind the cervix of the patient through the incision so that the distal end of the tube penetrates to the rectouterine pouch.

Preferably the method further comprises the steps of providing an elongated housing, positioning the tube and the uterus manipulator in the housing in a telescopically movable manner, preferably before positioning the tube and the uterus manipulator in the vagina.

Preferably the method further comprises the steps of repositioning the uterus by tilting the rotatable distal end of the uterus manipulator to a position making an angle 0 to 140 or 0 to 90 degree or 80 to 100 degree with the longitudinal axis of the tube, the angle being preferably 90 degree and locking the rotatable end of the uterus manipulator at the position.

Preferably the method further comprises the step of locking the tube and/or the uterus manipulator in the housing such that the tube and/or uterus manipulator can not be moved telescopically in the housing.

In another aspect of the present invention, a surgical apparatus for performing examinations and surgical interventions through the vagina and the rectouterine pouch of a female patient comprises a tube adapted to receive one or more surgical instruments there through and having a distal end with an oblique profile such that the distal end of the tube is inclined making an oblique angle with the longitudinal axis of the tube forming a nose at the distal end of the tube.

According to another feature of the present invention the distal end of the tube is covered by a cap portion having one or more holes adapted to receive the one or more surgical instruments there through, the cap portion having preferably a convex shape.

These measures have the advantage, among others, that the shape of the tube corresponds to the anatomical shape of the penis so that the apparatus is easy to introduce through the vagina and the rectouterine pouch. The oblique and convex shape of the penetrating distal end of the tube protects the rectum by keeping the rectum out of the penetration way.

According to another feature of the present invention the apparatus further comprises an elongated housing with a distal end such that the tube is telescopically movably arranged in the housing, the distal end of the housing preferably having an oblique profile such that the distal end of the housing is inclined making an oblique angle with the longitudinal axis of the housing, the housing preferably comprising a longitudinal slit.

According to another feature of the present invention the tube comprises one or more slits and/or grooves and/or rails and/or electrically conductive regions and/or magnetic regions on its outer surface.

According to another feature of the present invention the apparatus further comprises a uterus manipulator having a handle, a shaft extending from the handle and a rotatably distal end, the uterus manipulator preferably arranged longitudinally parallel to and movable with respect to the tube, preferably at the shortest longitudinal side of the tube and at the opposite side of the nose, the uterus manipulator preferably arranged in the housing in a telescopically movable manner.

According to another feature of the present invention the uterus manipulator comprises protrusions and/or one or more rail members and the uterus manipulator is slidably guided in one of the grooves.

According to another feature of the present invention an endobag or funnel shaped membrane is guided in one of the grooves and/or slits, the endobag or funnel shaped membrane preferably having guiding means, the guiding means preferably having one or more protrusions or a rail attached to the inner or outer surface of the endobag or funnel shaped membrane.

In accordance with an alternative embodiment of the present invention a surgical apparatus for performing examinations and surgical interventions through the vagina and the rectouterine pouch of a female patient comprises a tube adapted to receive one or more surgical instruments there through and a uterus manipulator having a handle, a shaft extending from the handle and a rotatably distal end, the uterus manipulator arranged longitudinally parallel to the tube.

In yet another aspect of the present invention, the uterus manipulator is introduced into the uterus through the vagina and serves to tilt the uterus in various directions. The hollow tube is able to receive one or more surgical instruments like graspers, scissors, clip applier, trocar, knife, vacuum, teneculum, light, visual apparatus, endobag, electrical apparatus, morcellator etc.

The features of uterus manipulators are widely known in the prior art and will not be disclosed here explicitly.

In accordance with a preferred embodiment of the present invention the uterus manipulator is arranged longitudinally movable with respect to the tube.

In accordance with a preferred embodiment of the present invention the tube comprises one or more slits and/or grooves and/or rails and/or electrically conductive regions and/or magnetic regions on its outer surface.

In accordance with a preferred embodiment of the present invention the uterus manipulator comprises protrusions and/or one or more rail members and the uterus manipulator is slidably mounted in one of the grooves.

In accordance with a preferred embodiment of the present invention the distal end of the tube is covered by a cap portion having one or more holes adapted to receive the one or more surgical instruments there through, the cap portion having preferably a convex shape.

In accordance with a preferred embodiment of the present invention the apparatus further comprises an elongated housing, the tube is telescopically movably arranged in the housing, the housing preferably comprising a longitudinal slit, the uterus manipulator and/or the tube preferably arranged in the housing in a telescopically movable manner.

In accordance with a preferred embodiment of the present invention an endobag or funnel shaped membrane is guided in one of the grooves and/or slits, the endobag or funnel shaped membrane preferably having guiding means, the guiding means preferably having one or more protrusions or a rail attached to the inner or outer surface of the endobag or funnel shaped membrane.

In yet another aspect of the present invention, an endobag for transporting body tissue through transvaginal-transdouglas route having guiding means is provided. The guiding means preferably includes one or more protrusions or a rail or a rod or a channel or a pipe attached to the inner or outer surface of the endobag. The endobag may be a funnel shaped membrane.

Further details of the present invention are defined in the appended pages, drawings and claims.

Advantageous Effects of the Invention

The present invention provides such a method and apparatus for a secure incision in the vaginal wall, preferably in the posterior fornix of the vagina, wherein uterine vessels and cardinal/uterosacral ligaments are accurately secured without causing any complication and prolongation of the operation.

The present invention provides such a method and apparatus for protecting the operation environment in the human body.

The present invention provides such a method and apparatus for protecting the rectum from being injured during the operation.

More particular, the present invention provides such a method and apparatus which may be used in laparoscopic surgery, preferably in natural orifice transluminal endoscopic surgery.

Further, the present invention provides such a method and apparatus which substantially minimizes trauma to the patient and reduces healing time.

These and other objects of the present invention will be apparent from the drawings, claims and detailed descriptions herein.

BRIEF DESCRIPTION OF THE DRAWINGS

The accompanying drawings, referred to herein and constituting a part hereof, illustrate preferred embodiments of the present invention and together with the description, serve to explain the principles of the present invention, wherein.

DESCRIPTION OF THE EMBODIMENTS

The present invention is contemplated to be used in surgical procedures where manipulation of body structures is required to provide access to the particular body structure or adjacent body structures. While the apparatus of the present invention is particularly useful for manipulation of the uterus, it will also be useful for treating other body organs and structures during other laparoscopic and non-laparoscopic surgical procedures.

Figure 1:
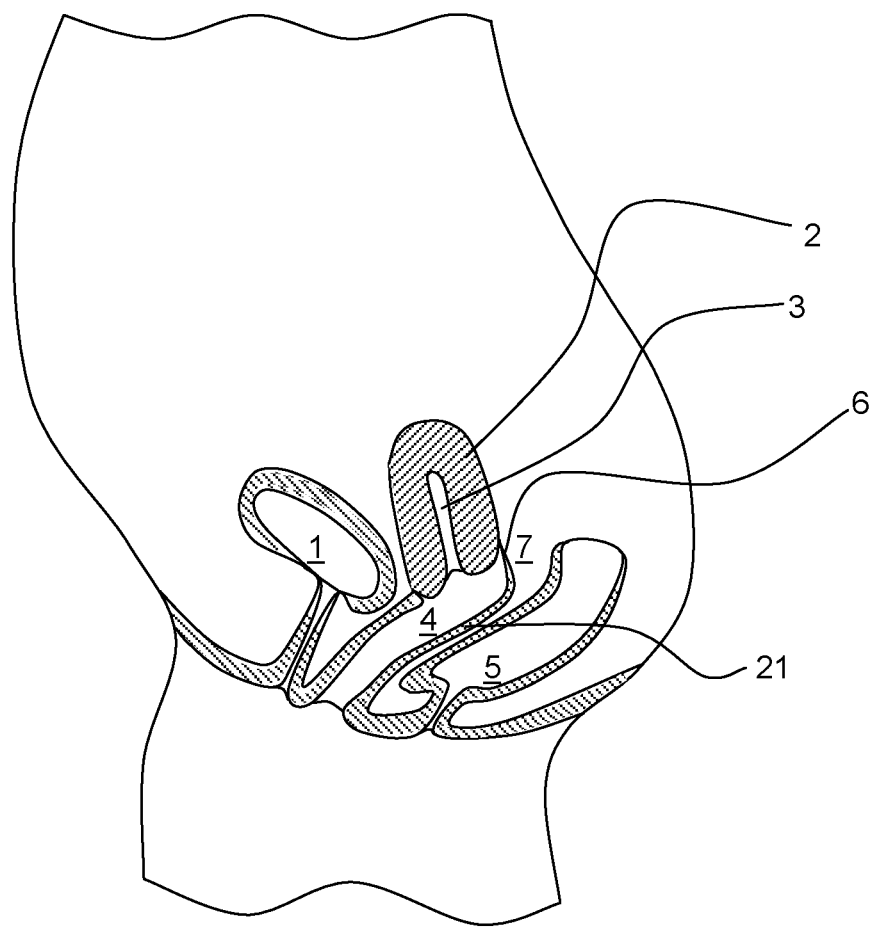
FIG. 1 is a partial cross-sectional view of a female body.
Figure 2:
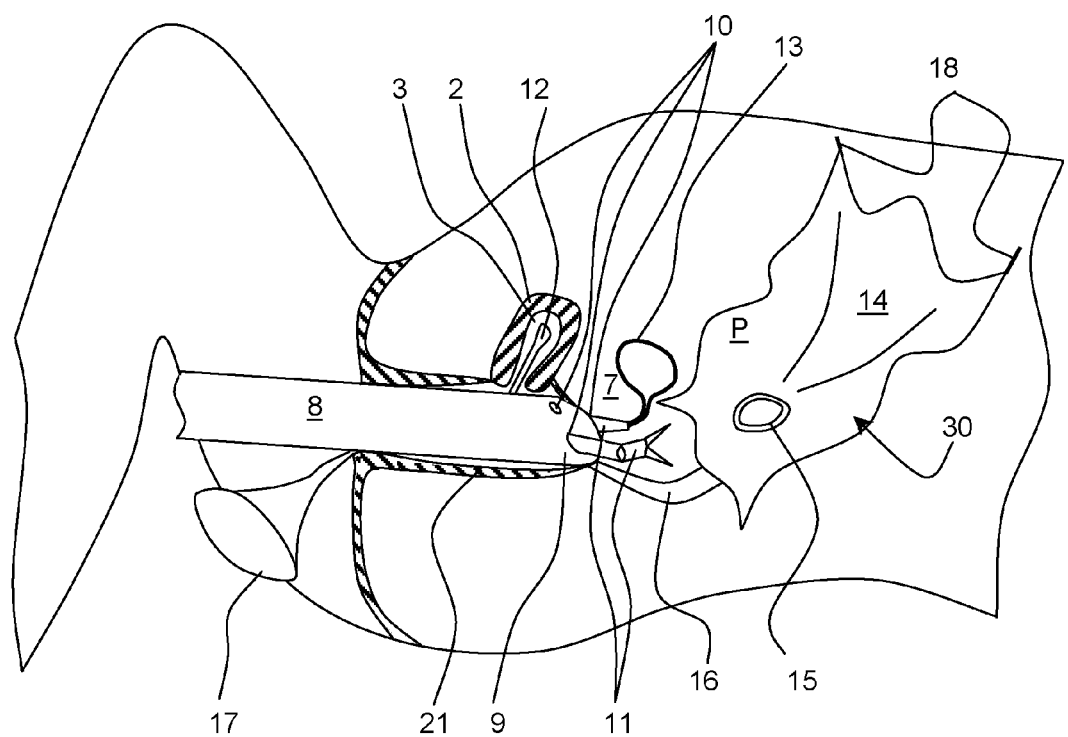
FIG. 2 is a view of an embodiment of the present invention placed in the female body.

Referring to FIG. 1, there is illustrated in cross-sectional view of a partial female body showing the transvaginal-transdouglas route.

FIGS. 2, 9, 10A, 10B and 10C show an embodiment of the apparatus constructed according to the present invention. The apparatus comprises an elongated body 8, 23, 27. The elongated body 8, 23, 27 has a proximal end and a distal end 9 that penetrates into the rectouterine pouch 7. The distal end 9 may be shaped oblique forming a nose. This shape may enable a smooth introduction of the apparatus into the transvaginal-transdouglas route. The elongated body has one or more channels 10. Different surgical instruments can be introduced through the channels 10. There is provided one or more longitudinal grooves 19 on the outer surface of the elongated body 8. A uterus manipulator 12 is guided in the upper groove 19 which faces the uterus when the apparatus is positioned in the vagina. The uterus manipulator 12 has a distal end 32 which is rotatable by moving or rotating a handle 33, 34 which will not be described here.

Figure 3A:
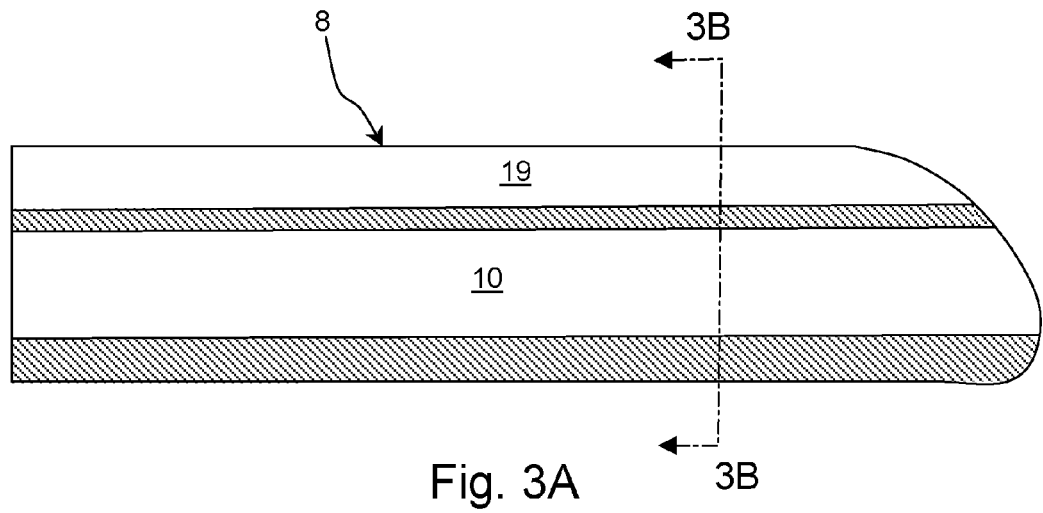
FIG. 3A is a cross-sectional side view of an embodiment of the present invention.
Figure 3B:
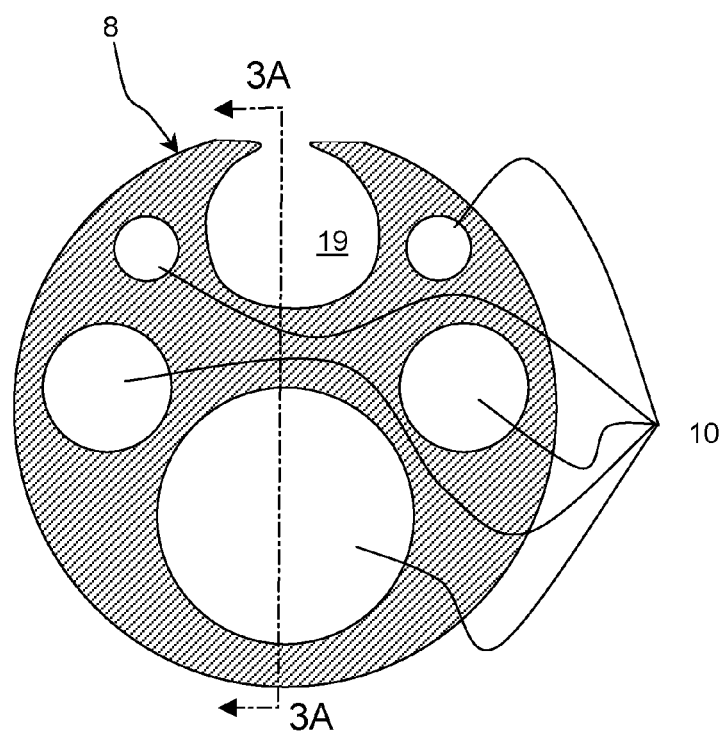
FIG. 3B is a cross-sectional frontal view of an embodiment of the present invention.
Figure 3C:
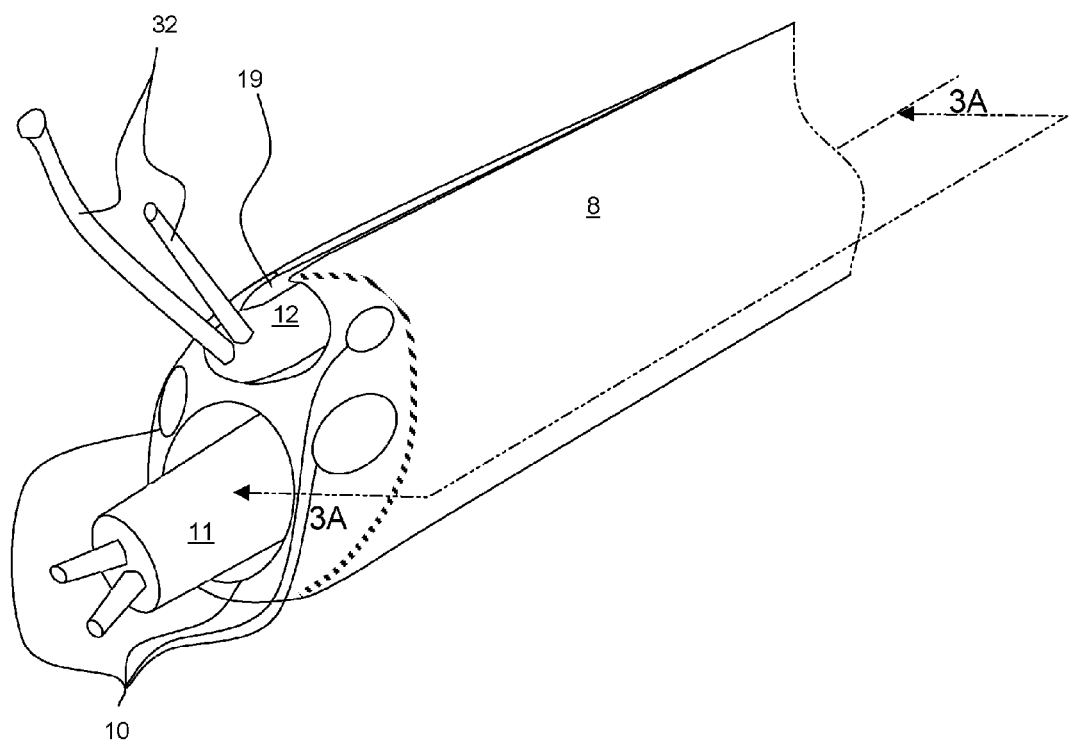
FIG. 3C is a perspective view of an embodiment of the present invention.

FIGS. 3A, 3B and 3C show an embodiment of the apparatus constructed according to the present invention.

Figure 4A:
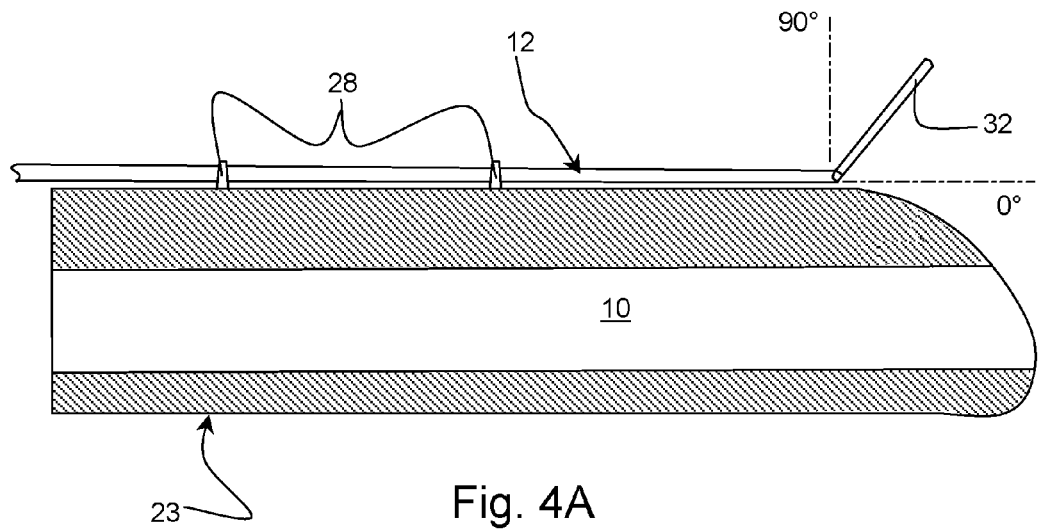
FIG. 4A is a cross-sectional side view of an alternative embodiment of the present invention.
Figure 4B:
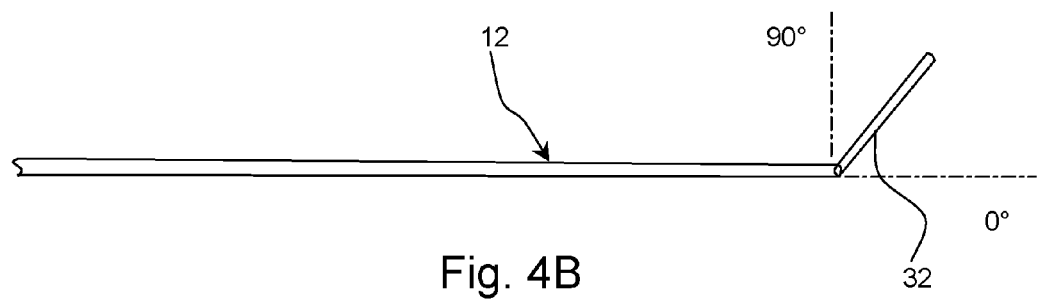
FIG. 4B is a side view of a surgical instrument according to the invention.

FIGS. 4A, 4B show an alternative embodiment of the apparatus constructed according to the present invention. The apparatus comprises a tube 8 and a uterus manipulator 12 is slidably attached to the apparatus. The tube 8 has a distal end 9 that penetrates into the rectouterine pouch. Different surgical instruments can be introduced through the tube 8.

Figure 5A:
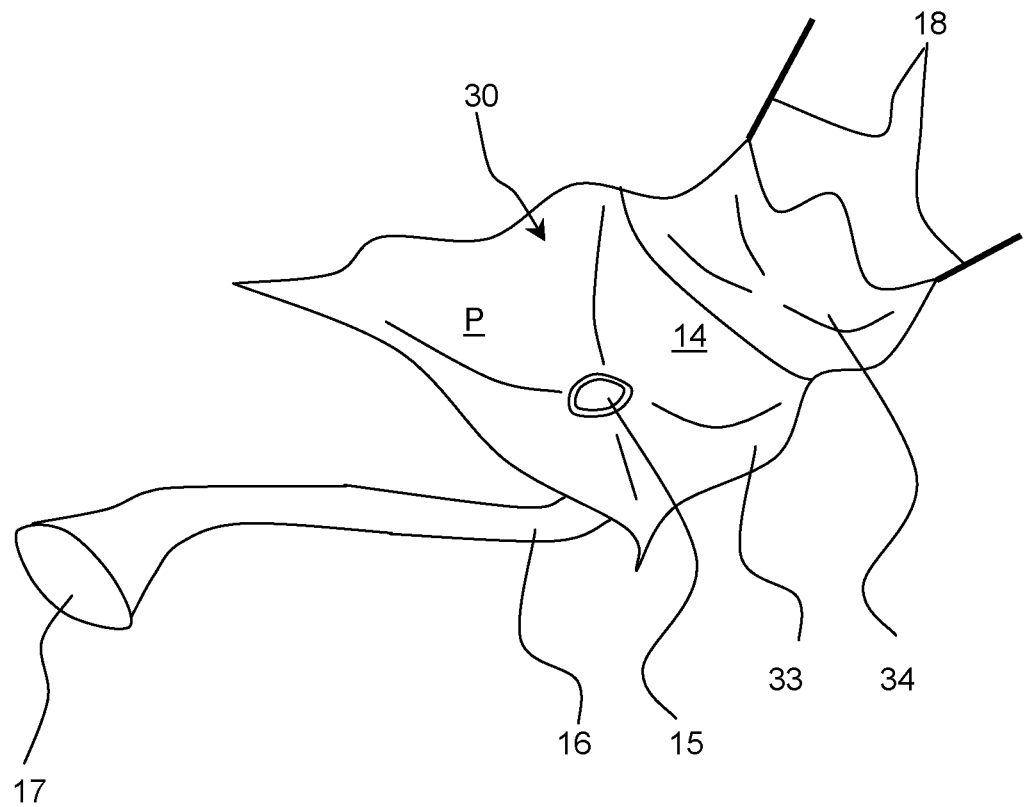
FIGS. 5A and 5B show alternative surgical bag embodiments according to the invention.
Figure 5B:
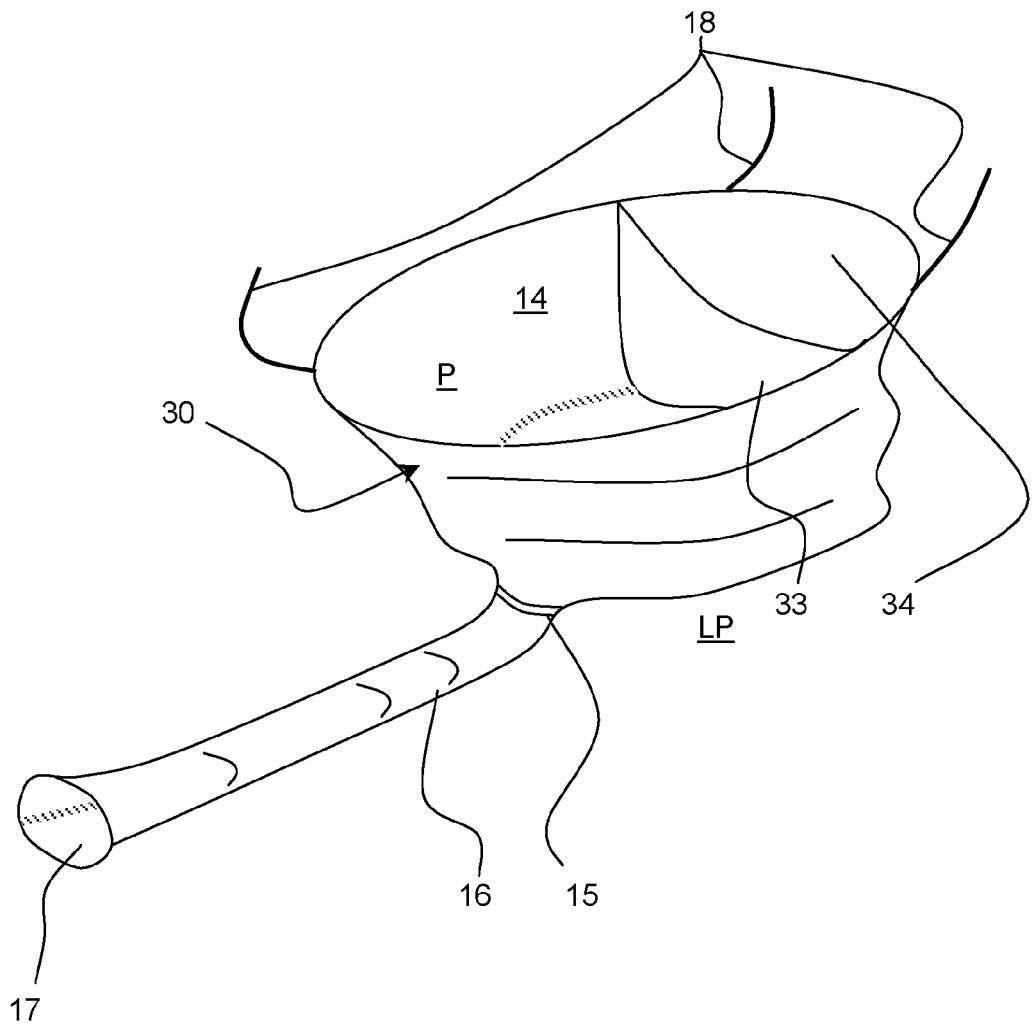
Figure 8:
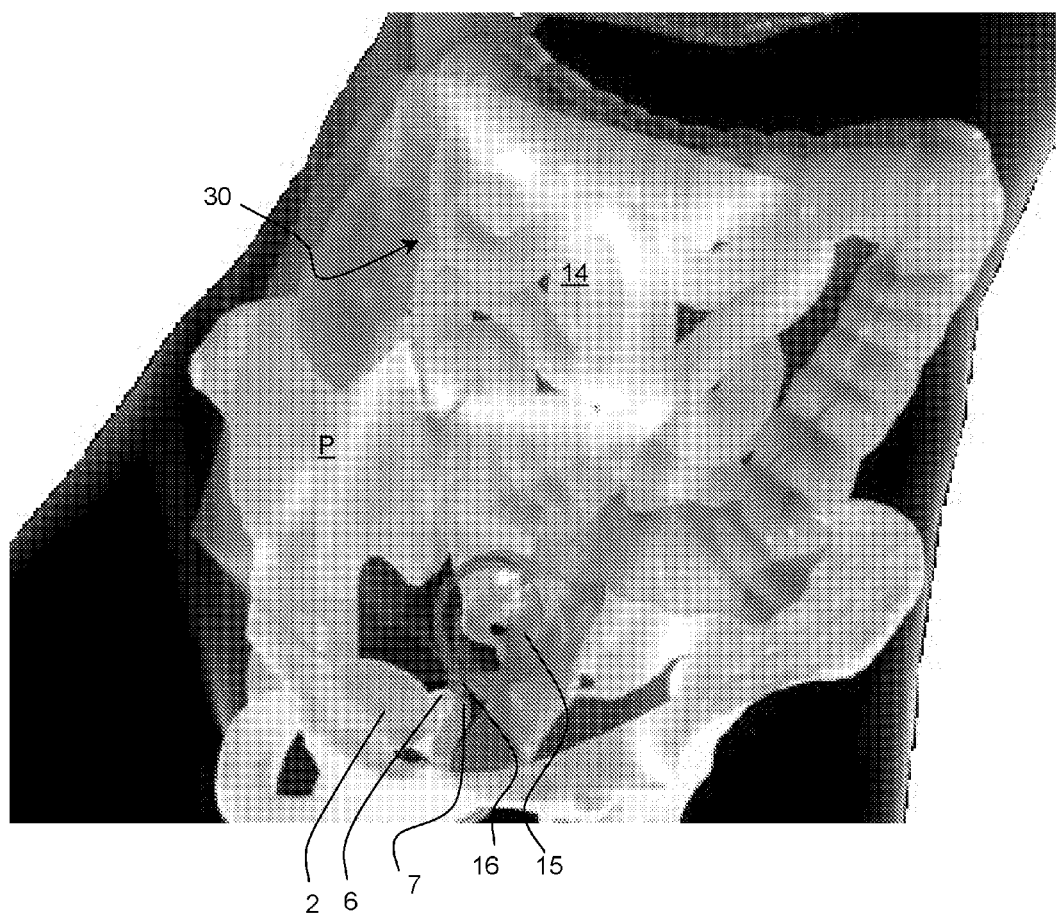
FIG. 8 is a partial cross-sectional view of a female body illustrating an embodiment of an endobag apparatus according to the invention.
Figure 9:
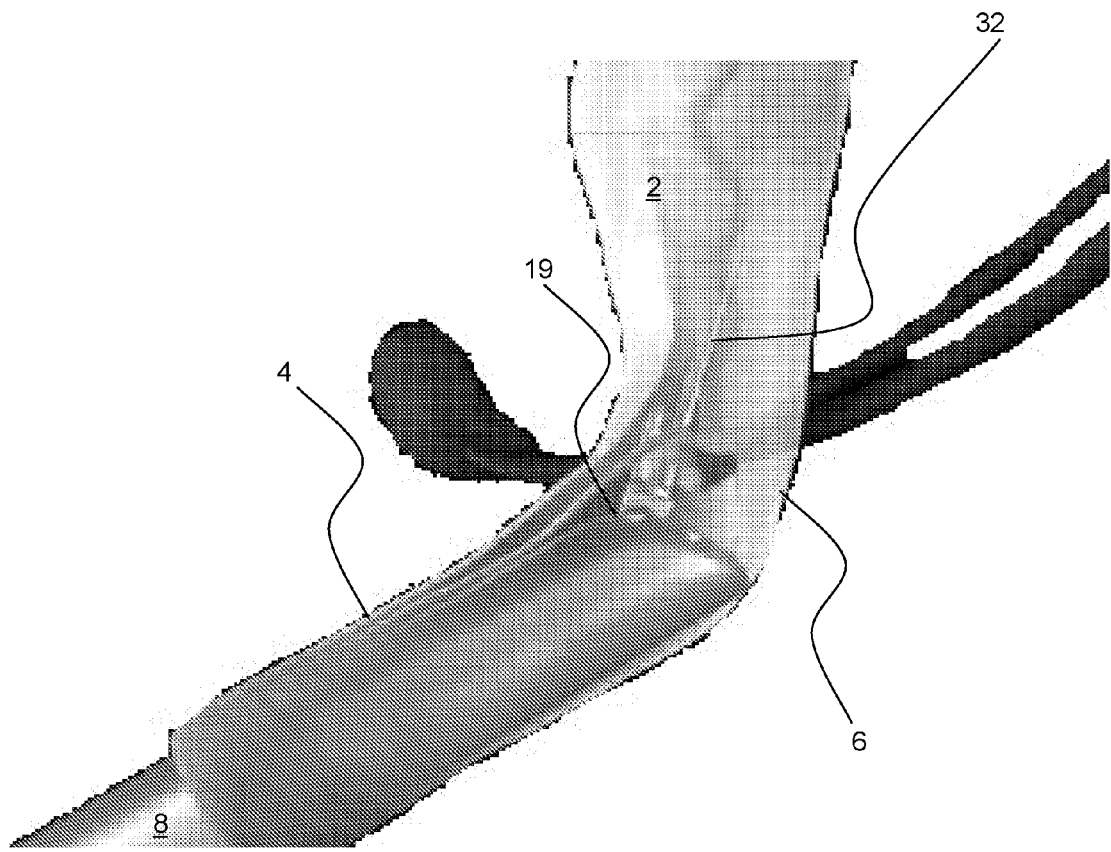
FIG. 9 is a partial cross-sectional view of a female body illustrating an embodiment of an apparatus according to the invention positioned in the vaginal canal.
Figure 10C:
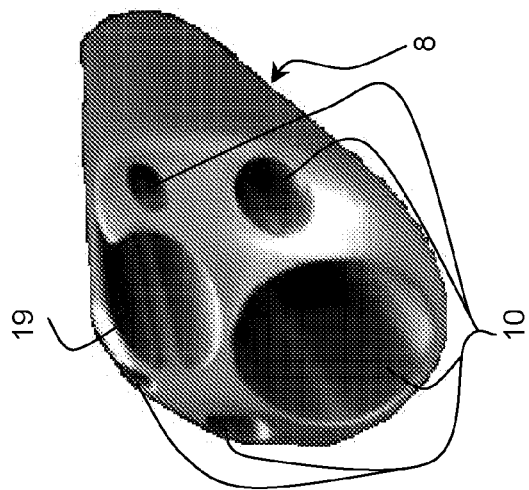
FIGS. 10A, 10B, 10C show the apparatus of FIG. 9 in side, frontal and perspective views.
Figure 10B:
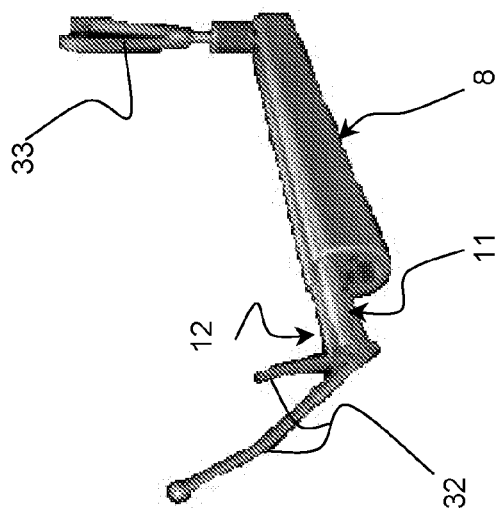
Figure 10A:
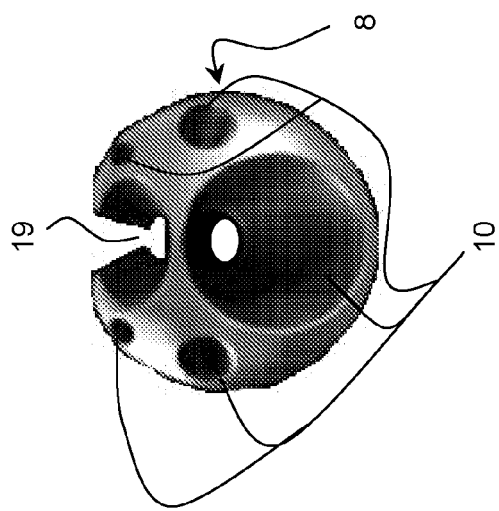

FIGS. 5A, 5B and 8 show an endobag 30 constructed according to the present invention. The endobag has an distal open end 14 which is placed through the rectouterine pouch 7 and a proximal open end 17. Body tissues can be transported through the endobag 30. The distal open end 14 of the endobag 30 may have a funnel shape.

Figure 6A:
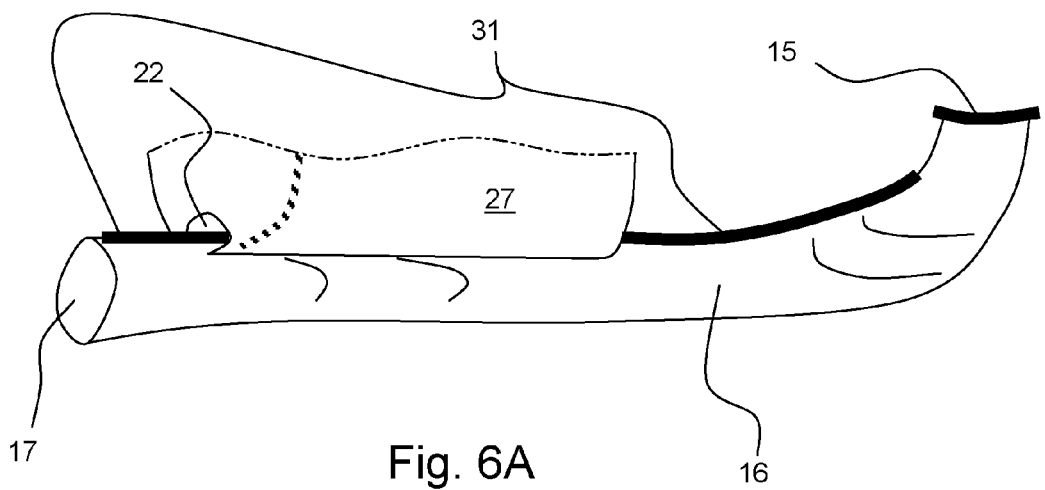
FIG. 6A is a partial view of an alternative surgical bag embodiment and an alternative embodiment of the apparatus according to the invention.
Figure 6B:
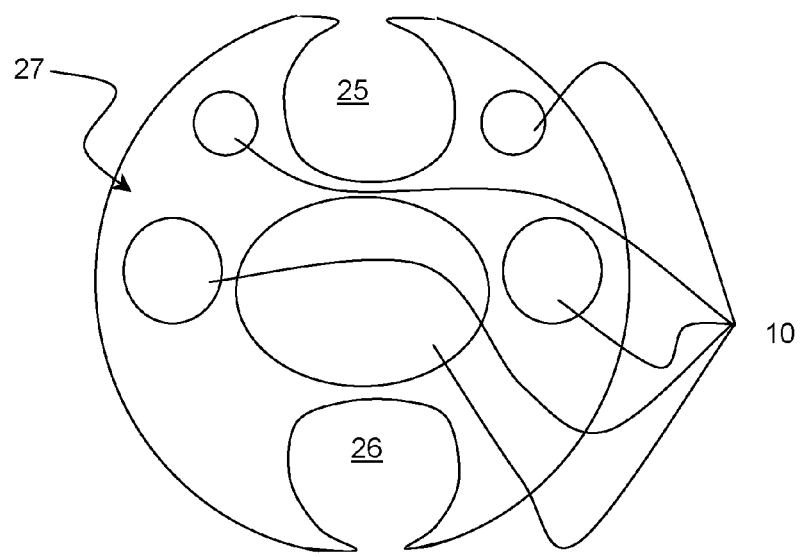
FIG. 6B is a frontal view of the apparatus of FIG. 6A.

FIGS. 6A, 6B show another embodiment of the endobag apparatus constructed according to the present invention. The endobag is guided in a lower groove 26 of an elongated body 23. The endobag may have guiding means 31 which can slide in the lower groove 26.

Figure 7A:
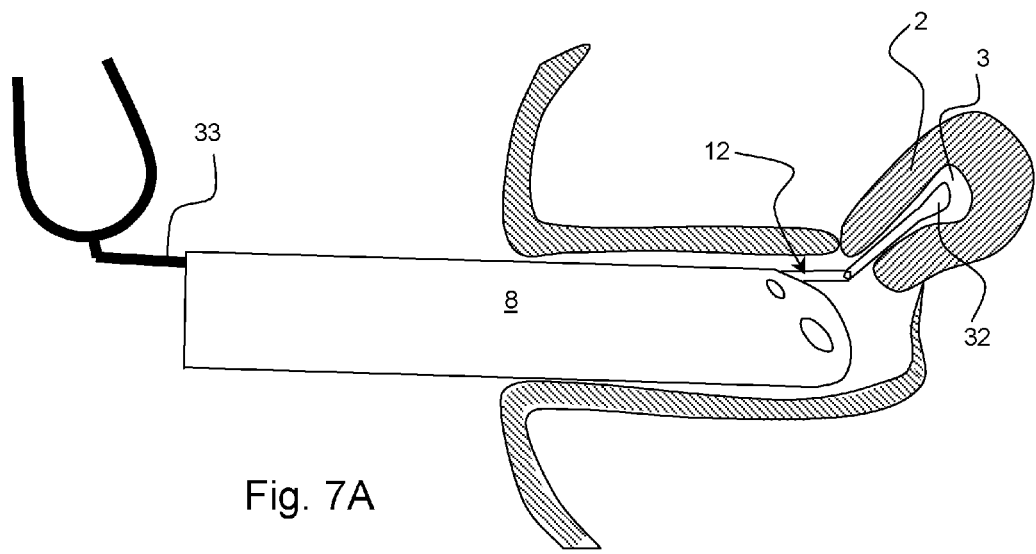
FIG. 7A is a partial cross-sectional view of a female body with an embodiment of the present invention positioned in the vaginal canal in a first position.
Figure 7B:
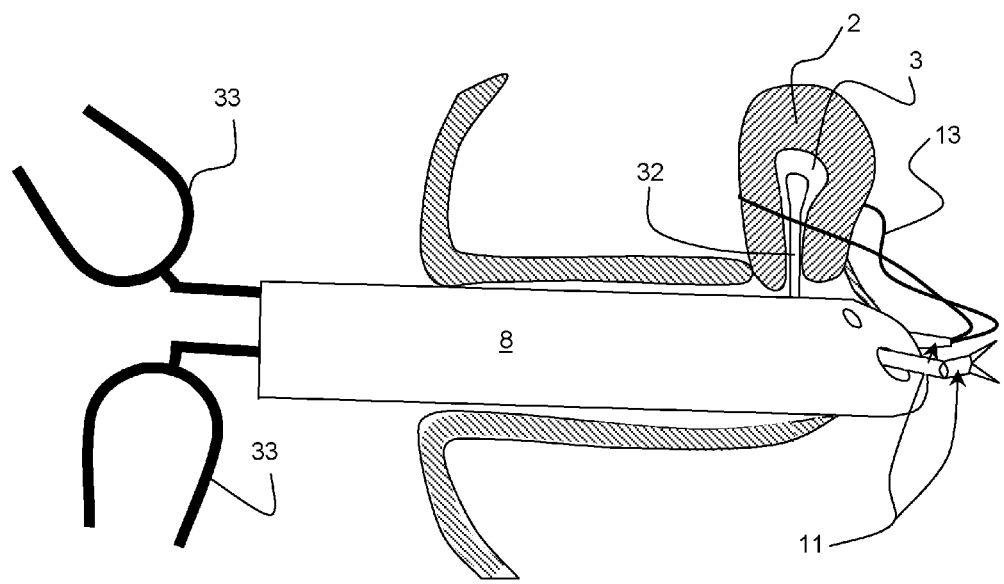
FIG. 7B is a partial cross-sectional view of a female body with an embodiment of the present invention positioned in the vaginal canal in a second position.

FIGS. 7A, 7B show an embodiment of the apparatus constructed according to the present invention positioned in the vagina 4. The distal end 32 of the uterus manipulator 12 is introduced into the uterus 2, is tilted 90 degree with respect to the elongated body 8 and the elongated body 8 is slided with respect to the uterus manipulator 12 through the vagina 4. The distal end 9 of the elongated body 8 is penetrated through the rectouterine pouch 7. One or more surgical instruments 11 are placed through the holes in the distal end 9 of the elongated body 8.

While the above description contains many specifics, these specifics should not be construed as limitations on the scope of the invention, but merely as exemplifications of preferred embodiments thereof. Those skilled in the art will envision many other possible variations that are within the scope and spirit of the invention as defined by the claims appended hereto.

List of Key Features of the Invention:
Uterine Arteries sutured after Corpus Uteri amputation
Steps Part 1
    Insuflation
    One Skin Incision Umbilical
    One Port multichannel (3 mm×2 or 5 mm+3 mm)
    Two 3 mm×2 or 5 mm+3 mm Step O
  Notes Uterine Manipulator Crania-Caudal
  Rotation Lateral-Medial, 0 to 90 degree Antireflection
  Multi-channel Round/Elliptical barrel 8 with a groove 19 that accommodates Slides 12 in the Rounded Shaft of Pelosi/Valchev Uterine Manipulator Concept
Properties of the Barrel 8
Future
Single Site Surgery
Notes
  Barrel 8
  Solid and Flexible (durable rubber) that accommodates different size operative instruments 11 namely to function as uterine artery suture 13 and occlusion system
  Introduction Flexible Tip Camera
  Introduction and execution of Cervico-Corporal Amputation System 13 (Lina Loop, Lap Loop, and similar Storz kind)
  Accommodate or Introduction of Irrigation and Suction, Anti adhesive and Anti Bacterial
  Barrier Gel and Spray system
  Accommodate or Introduction of Multiple Vaginal Ports and Tracers both solid and flexible
  To access and operate in peritoneal and retroperitoneal space and organs kidney, bowel, liver, appendix, spleen, artery, vein, pancreas transvaginally.
  Accommodate or Introduction Morcellator (Straight Knife and Circular Motorized)
  Accommodate or Introduction Morcellator Laparachute Bag system 30
Laparachute
  Transvaginal collecting bag system 30 that deploys in pelvic cavity to baloon into the upper peritoneal cavity, for the purpose better visual operative space, to protect bowel and other intraperitoneal organs from infection, cancer that may be spilling from the specimen or other sources; bag (in a secondary compartment) that contains the spillage or irrigation fluid system to drain continuously to an external collection bag system.
Steps Part 2
  Uterine Arteries Transcervical (Single Choking Loop Suture)
  Amputation-Corpus Uteri Detachment (Vaginal)
  Lap Loop
  Lina Loop
  Morcellation Vaginal
  Bags Vaginal
Uterine Artery Single Choking Loop Suture 13
  Posterior endocervical insertion of a suture 13 into peritoneal cavity, the path following through avascular broad ligament leafs, circumventing the anerious cervix 2 anagain piercing through the contralateral brad ligament leaf then being grabbed transcervically, pulled out tied into the cervical canal, where the knots get buried.

The invention claimed is:

1. A method for use in a pelvic or peritoneal surgery comprising the steps of:
  providing an apparatus through the vagina and the rectouterine pouch of a patient, said apparatus comprising:
  a bag portion adapted to be placed inside the body of the patient and adapted to receive body tissue to be removed during the surgery, said bag portion having an opening for body tissue removal, wherein said apparatus is configured such that said bag portion can be placed inside the body of the patient by applying pressure to said bag portion,
  inserting said bag portion in a closed configuration through the vagina and the rectouterine pouch into a peritoneal cavity of the patient, applying pressure into the pelvic cavity such that said bag portion is opened, placed, and fixed to an interior of the body in the pelvis by introducing pressurized liquid or gaseous medium into the pelvis.

2. The method according to claim 1, wherein said pressurized liquid or gaseous medium is introduced into the pelvis through at least one of the vagina and said apparatus.

3. The method according to claim 1, wherein the pressure above and/or inside said apparatus is set higher than the pressure below and/or outside said apparatus so that said apparatus is placed and fixed inside the human body with the help of the pressure difference, wherein the pressure above and/or inside and/or below and/or outside said apparatus is adjusted by said liquid or gaseous medium which is transferred to inside of the human body.

4. The method according to claim 1, wherein attachment means are provided at said bag portion, for attachment to the body or to a surgical apparatus and said attachment means are attached to the to the body or to a surgical apparatus such that said bag portion is placed in the pelvis.

5. The method according to claim 1, further comprising the steps of:
  providing a uterus manipulator having a rotatable distal end into the vagina of the patient;
  placing said rotatable distal end of said uterus manipulator into the uterus and repositioning the uterus using said rotatable distal end to an appropriate positions to make an incision in the posterior fornix of the vagina;
  making an incision in the posterior fornix of the vagina to introduce said apparatus through the vagina and the rectouterine pouch through an elongated body of a surgical apparatus.

* * * * *